(12) United States Patent
Takada

(10) Patent No.: US 7,695,729 B2
(45) Date of Patent: *Apr. 13, 2010

(54) NONORAL PREPARATION HAVING THREE-LAYER STRUCTURE

(76) Inventor: Kanji Takada, 618-2, Gokoumachidori Gojoagaru Azuchi-cho, Shimogyo-ku, Kyoto-shi, Kyoto 600-8040 (JP)

( * ) Notice: Subject to any disclaimer, the term of this patent is extended or adjusted under 35 U.S.C. 154(b) by 1498 days.

This patent is subject to a terminal disclaimer.

(21) Appl. No.: 10/275,973

(22) PCT Filed: May 24, 2001

(86) PCT No.: PCT/JP01/04355

§ 371 (c)(1),
(2), (4) Date: Mar. 21, 2003

(87) PCT Pub. No.: WO01/89486

PCT Pub. Date: Nov. 29, 2001

(65) Prior Publication Data

US 2003/0157140 A1    Aug. 21, 2003

(30) Foreign Application Priority Data

May 26, 2000    (JP)    ............... 2000-156227

(51) Int. Cl.
*A01N 63/00* (2006.01)
*A01N 65/00* (2009.01)
*A61K 38/28* (2006.01)
*A61K 38/24* (2006.01)
*A61K 38/20* (2006.01)
*A61K 35/78* (2006.01)
*A61K 9/70* (2006.01)
*A61K 45/00* (2006.01)
*A61K 39/08* (2006.01)

(52) U.S. Cl. .............. 424/422; 424/449; 424/736; 424/239.1; 424/85.2; 424/93.7; 424/405; 514/2; 514/3

(58) Field of Classification Search .............. None
See application file for complete search history.

(56) References Cited

U.S. PATENT DOCUMENTS

| 3,516,941 | A | * | 6/1970 | Matson ............... 264/4.33 |
| 3,926,188 | A | * | 12/1975 | Baker et al. ............... 424/427 |
| 4,765,983 | A | | 8/1988 | Takayanagi et al. |
| 5,236,713 | A | | 8/1993 | Wato et al. |
| 5,633,002 | A | * | 5/1997 | Stricker et al. ............... 424/426 |
| 5,900,247 | A | | 5/1999 | Rault et al. |
| 6,858,581 | B2 | * | 2/2005 | Kuhner et al. ............... 514/2 |
| 7,090,861 | B2 | * | 8/2006 | Brines et al. ............... 424/422 |
| 7,097,851 | B1 | * | 8/2006 | Takada ............... 424/435 |

FOREIGN PATENT DOCUMENTS

| EP | 1135112 | 10/2004 |
| JP | 58-11135 | 1/1983 |
| JP | 58126815 | 8/1983 |
| JP | 5-43453 | 2/1993 |
| JP | 10182442 | 7/1998 |
| WO | 98/24412 | 6/1998 |
| WO | 00/32172 | 6/2000 |
| WO | WO 00/32172 A1 * | 6/2000 |

* cited by examiner

*Primary Examiner*—Robert A Wax
*Assistant Examiner*—Danah Al-Awadi
(74) *Attorney, Agent, or Firm*—Greenblum & Bernstein, P.L.C.

(57) ABSTRACT

The purpose of the present invention is to provide micro- or mili-capsules and film preparations having not only sustained-release function but also targeting and adhesive functions with approximately 100% loading efficiency of the objective substance. The present invention provides a parenteral preparation having three layers structure of; basement layer composed of polymer; carrying layer that contains objective substances selected from drugs, aroma chemicals, mosquito propellant, dyes, cells or antigens; and surface layer, and in which the carrying layer is sandwiched between the basement layer and the surface layer.

**5 Claims, No

NONORAL PREPARATION HAVING THREE-LAYER STRUCTURE

TECHNICAL FIELD

The present invention relates to a parenteral preparations of asymmetric micro-capsules, mili-capsules or films composed of three layers, that can contain objective substance with approximately 100% loading efficiency, as well as the method for producing them.

BACKGROUND ART

In the conventional methods to prepare microcapsules such as solvent evaporation method from W/O type, O/W type or W/O/W type emulsions for the purpose of stabilizing unstable compounds or releasing the incorporated compounds at a constant rate, only almost spheric and symmetric microcapsules can be produced.

The present inventor previously innovated the asymmetric (hemisperical) micro- or mili-capsules having three-layers structure as pharmaceutical preparation (Kanji Takada, International Application No. PCT/JP99/06602, An oral formulation for gastrointestinal drug delivery). By means of the conventional preparation methods of microcapsules, those micro- or mili-capslues cannot be produced in large scale. In addition, it is impossible to attain the complete loading efficieny (almost 100%) of the objective substance inside the micro-capsules. The conventional preparing methods of micro-capsules have a low loading efficiency of the objective substance inside the micro-capsules, and have a low recovery due to the wide variation of the particles size of the obtained micro-capsules.

Many preparation methods of micro-capsules including solvent evaporation method from W/O/W emulsions have been developed up to now. However, the micro-capsules obtained by these techniques have spherical shapes. Also, in the conventional methods, it was extremely difficult to load the objective substance into the micro-capsules with loadimg efficiency of 100%.

DISCLOSURE OF THE INVENTION

The present inventor previously innovated an oral gastrointestinal mucoadhesive patch system having three layers structure (Kanji Takada, International Application No. PCT/JP99/06602, An oral formulation for gastrointestinal drug delivery). This oral mucoadhesive patch system concerns the film preparation and hemispherical micro- or mili-capsules for nonparenteral administration. However, we must develop a method for producing hemispherical micro- and mili-capsules or film preparation to produce large amount of the parenteral preparations with high loading efficiency which contain objective substance selected from drugs (except orally well-absorbable drugs), aroma chemicals (aromatic substance), mosquito repellant, cells (for example artificial cells and the like) or antigens.

An object of the present invention is to provide micro- or mili-capsules and film preparations having not only sustained-release function but also targeting and adhesive functions with approximately 100% loading efficiency of the objective substance, as well as the method for producing the same. Another object of the present invention is to provide the method of producing the large amount of the above mentioned preparations.

The present inventor found out that above objects can be solved by producing hemisphrical micro- or mili-capsules and film preparations having a three layers structure composed of a basement layer, a carrying layer containing objective substance and a surface layer, and have made this invention.

Thus, the present invention provides a parenteral preparation having three layers structure of; basement layer composed of polymer film; carrying layer that contains objective substances selected from drugs, aroma chemicals, mosquito repellant, dyes, cells or antigens; and surface layer, and in which the carrying layer is sandwiched between the basement layer and the surface layer.

In one embodiment of the present invention, the basement layer, the carrying layer and the surface layer are each film, and these three layers are laminated.

In another embodiment of the present invention, the basement layer is a hemispherical form, the carrying layer is present in the space inside the hemispherical form, and the opening of the hemispherical form is covered with the surface layer.

Preferably, the polymer of the basement layer is water-insoluble polymer or biodegradable polymer.

Preferably, the basement layer is a film made of ethylcellulose, cellulose acetate, polylactic acid, poly(lactic-co-glycolic acid) hydroxypropyl methylcellulose phthalate or methacrylic acid copolymer S (Eudragit S).

Preferably, the objective substance contained in the carrying layer is granulocyte colony-stimulating factor (G-CSF), erythropoietin, interleukins, growth hormones, calcitonin, insulin, orange oil, N,N-diethyl-m-toluamide, botulinum toxin or pancreartic islet cells.

Preferably, the surface layer is made of pH-sensitive polymer, water-insoluble polymer or biodegradable polymer.

The present invention provides a method of producing a parenteral preparation, which comprises the steps of:

forming micron- or mili-size dents on the basement layer made of a film prepared by using water-insoluble polymer or biodegradable polymer;

filling an objective substance selected from drugs, aroma chemicals, mosquito repellant, dyes, cells or antigens in the said dents;

sealing the openings of the dents by adhering the surface layer made of a polymer film on which adhesive glue is painted onto the top of the dents; and cutting the obtained three-layered film into micron- or mili size, as well as a parenteral preparation produced by said method of producing.

The present invention also provides a method of producing a parenteral preparation, which comprises the steps of:

spreading a mixture of an objective substance selected from drugs, aroma chemicals, mosquito repellant, dyes, cells or antigens and an adhesive agent on the basement layer made of a film prepared by using water-insoluble polymer or biodegradable polymer;

covering the top of the thus spread mixture with the surface layer made of polymer film; and sealing and punching out the three layered polymer film with a pre-heated hole puncher having a μm or mm size holes, as well as a parenteral preparation produced by said method of producing.

BEST MODE FOR CARRYING OUT THE INVENTION

The three layered parenteral preparations of the present invention can be produced in a large scale by, for example;

forming a basement layer having dents of which size is in the order of μm or mm; filling an object substance selected from drugs, aroma chemicals, mosquito repellant, dyes, cells or antigens in the dents; sealing with a surface film on which adhesive glue is painted; and cutting the film into micron- or mili size.

When the object substance is tolerable to the heating process, three layered micro- or mili-capsules and film preparations can be produced by; mixing an object substance selected from drugs, aroma chemicals, mosquito repellant, dyes, cells or antigens with an adhesive agent; spreading the resultant mixture onto a film (a basement layer) prepared by using water-insoluble polymer, biodegradable polymer or the like; covering the adhesive layer with various polymer film (a surface layer); and heat pressing and punching out the three layered film with a heated hole puncher having μm or mm size hole.

The parenteral preparation of the present invention has three layers structure of basement layer, carrying layer and surface layer, and is preferably provided as asymmetric micro- and mili-capsules or film preparations.

The basement layer is a bowl-like container having μm or mm dents which is made of water-insoluble polymer or biodegradable polymer, and has a function of protecting the included objective substance or controlling the release rate of the included objective substance.

In the aforementioned container having μm or mm size dents, carrying layer is formed to make a space to contain an objective substance selected from drugs aroma chemicals, mosquito repellant, dyes, cells or antigens (vaccine).

To increase the retention of the objective substance in the carrying layer, sponge made of cellulose, tissue paper or fibers can be added.

The surface layer is a film made of various polymer for protecting the leakage of the objective substance from the μm or mm size dents, and obtaining the adhesiveness to the target site. Examples thereof include hydroxypropyl methylcellulose phthalate (HP-55) which dissolves by the environmental pH change, methacrylic acid copolymer L (Eugragit L), methacrylic acid copolymer LD (Eugragit LD), and methacrylic acid copolymer S (Eugragit S).

The thickness of the surface layer is not particularly limited. For example, the thickness is about 10-100 μm, preferably about 20-70 μm, more preferably about 30-50 μm.

The polymers used for the basement layer are water-insoluble polymer such as ethyl cellulose, aminoalkyl methacrylate copolymer-E (Eudragit E), aminoalkylmethacrylate copolymer (Eudragit RS) cellulose acetate, chitin and chitosan, and biodegradable polymers such as polylactic acid.

The thickness of the surface layer is not particularly limited. For example, the thickness is about 10-100 μm, preferably about 20-70 μm, more preferably about 30-50 μm.

The basement layer is either a film or a film having dents. In the case of dents, the size is preferably the order of μm or mm, where the depth is 10-1000 μm and the diameter is 20-80 μm. When dents are formed from film, a film is at first made by casting the polymer solution dissolved in organic solvent such as ethyl alcohol onto the Teflon plate, and evaporating the solvent. For example, 550 mg of ethyl cellulose and 25 μl of triethyl citrate are dissolved in 5 ml of a mixture of methylene chloride and methyl alcohol (4:1) and the solution is casted onto the Teflon plate. The obtained film is placed for several hours under heating with high temperature on a metal plate which has several hundred μm to several mm length sticks which are regularly arranged. After the film is cooled, many dents are formed where the depth is 10-1000 μm and the diameter is 20-8000 μm.

To fill an objective substance selected from drugs, aroma chemicals, mosquito repellant, dyes, cells or antigen into the micron- or mili-size dents, there are two methods, that is, solid phase method and liquid phase method.

In the case of solid phase method, an objective substance is mixed with adhesive agents which is an adhesive polymer such as carboxyvinyl polymer, copolymer of polyacrylate/octylacrylate, copolymer of 2-ethylhexyl acrylate/vinylpyrrolidone, copolymer resin of cyclofibroin acrylate, macrogol, copolymer resin of methyl acrylate/2-ethylhexyl acrylate, gum arabic, polyvinyl alcohol, polyvinylpyrrolidone, methylcellulose, hydroxypropylmethyl cellulose, polyisoprene, polyacrylic acid, sodium polymethacrylate, alginic acid, pregelatinized starch, carboxymethyl cellulose, sodium carboxymethyl starch, crystalline cellulose and cyclodextrins or gums, and given quantity of them are filled inside the μm or mm size dents in a solid state.

For liquid phase method, an objective substance and the adhesive agent are dissolved with the solvent for solving such as water to prepare a solution, and the resulting solution is filled in the micro- or mili-size dents in a liquid state by nano-injector or micro-injector.

As a surface layer, film of which thickness is 30-50 μm and is made of pH-sensitive polymer such as hydroxypropyl methylcellulose phthalate (HP-55), hydroxypropyl methylcellulose trimellitic acid (HPMCT), methacrylic acid copolymer L (Eugragit L), methacrylic acid copolymer LD (Eugragit LD), methacrylic acid copolymer S (Eugragit S), aminoalkyl methacrylate copolymer-E (Eudragit E;) and polyvinyl acetal diethyl aminoacetate, can be used. For example, 225 mg of HP-55 (Shinesu Chemicals Ltd.) and 25 μl of triethyl citrate are dissolved with 5 ml of a mixture of methylene chloride and methyl alcohol (4:1), and the solution is casted on a Teflon plate (10×10 cm). The resulting film is used for the surface layer. Also, as an example, 225 mg of Eudragit S100 or Eudragit L100 and 25 μl of triethyl citrate are dissolved with 5 ml of a mixture of methylene chloride and methyl alcohol (1:1), and the solution is casted on a Teflon plate. The resulting film is also used for the surface layer.

When the surface layer needs only sustained-release function and does not need the targeting function to the adhesive site, a film made of water-insoluble polymer such as ethylcellulose or biodegradable polymer such as polylactic acid can be used as the surface layer where the thickness of the membranes is 30-60 μm. In addition, a film made of water-insoluble polymer such as aminoalkyl methacrylate copolymer RS (Eugragit RS) and polyvinyl acetate resin can be used.

To seal the micron- or mili-size dents with surface layer, a solution of an adhesive glue such as Carbopol, Polycarbophil, Hiviswako, Noveon, sodium polyacrylate, poly-N-vinylacetamide (PNVA), polyvinylalcohol, copolymer of acrylate/octylacrylate, copolymer of 2-ethylhexylacrylate/vinylpyrrolidone, copolymer resin of cyclofibroin acrylate, gum arabic, pregelatinized starch, carmellose, hydroxyethyl cellulose, hydroxypropylcellulose, copolymer of metharylic acid/n-butyl acrylate is painted on the surface layer film, and is adhered to the dents containing the objective substance.

When the objective substance is heat-tolerable, the micron- or mili-size dents need not be formed on the basement layer. The objective substance is mixed with the adhesive agent, and the resulting mixture is spread on to a film (abasement layer) made of water-insoluble polymer or biodegradable polymer film. Next, the adhesive layer is covered with the surface film. Finally, by pressing and rotating with a heated hole puncher having sharp edge on the top of which size is several hundred µm or several mm, the polymer film is pressed and cut to prepare micron- or mili-size capsules and films. Also, micron- or mili-size capsules and films can be prepared by rotating a Teflon bar on the said three layers film that is placed on a heated plate having 10 to several hundred punching out pipes of which tops have sharp edges, and pressing and cutting said three layers film. Alternatively, the polymer films of basement layer and surface layer are cut into a rectangular shape, 3 mm×1 m. The basement film is placed on the surface film and the two sides are sealed by a heat-press sealing equipment with the sealing width of about 0.2 mm. In addition, sealings of which width is 0.2 mm are performed at the intervals of 3 mm, totally 330 seals are obtained. After the rectangular film was cut to 330 small bags, the mixture of the objective substance and the adhesive agent is filled and the openings were sealed by heat-press sealing method.

When objective substance is filled in micro- or mili-size dents that are formed on the basement layer, hemispherical micro- or mili-capsules or film preparations are obtained by cutting each capsule with laser beam or mechanical cutting machine.

When absorption enhancing agent such as citric acid, polyoxyethylene hydrogenated castor oil derivatives, capric acid, and ursodeoxycholic acid is formulated in the carrying layer with recombinant protein drug such as G-CSF, insulin, calcitonin, erythropoietin and growth hormones, the bioavailability of protein/peptide drugs can be increased.

Aroma chemicals, mosquito repellant, cosmetic dyes and the like are mixed with gel-forming polymer to prepare a carrying layer, and the resulting mixture is sandwiched between the surface layer and the basement layer. Consequently, micro- or mili-capsules and film preparations can be obtained by pressing and punching out with a pre-heated hole puncher.

When living cells such as pancreatic islet cells are filled inside the micro- or mili-size dents, artificial organ can be prepared with approximately 100% loading efficiency of the objective cells. Also, micro- or mili-capsules containing vaccine can be prepared with high loading efficiency by filling botulinum toxin or DNA vaccine in the micro- or mili-size dents.

The parenteral preparations of the present invention can be applied to humans or animals by the following several administration routes except oral route; rectal, vaginal, intravenous, muscle, subcutaneous, ocular, peritoneal, nasal and the like routes. In some cases, said parenteral preparaetion can be administered onto the skin surface as skin patches.

The present invention will be further illustrated by the following examples. It is to be understood that the present invention is not limited to these examples.

EXAMPLES

Example 1

550 mg of ethylcellulose (EC) and 25 µl of triethyl citrate were dissolved with 5 ml of a mixture of methylene chloride and ethyl alcohol (4:1). The resulting mixture was spread on the Teflon plate of which size was 10×10 cm. By evaporating the solvent, EC film of which thickness was about 50 µm was obtained. Many dents were prepared by pressing the EC film for 30 minutes with steel lump, 10 kg, on a aluminium plate (9 cm×3.5 cm), coated with small amount of liquid paraffin and heated to 90° C., that has 1000 projections (20×50) of which diameter was 200 µm and height was 100 µm.

EC film having many dents were obtained by removing from the aluminium plate after it was cooled. 50 nl of N,N-diethyltoluamide(Tokyo Kasei, Co. Ltd.), malaria repellant, was injected into each dents by a nanoinjector. 2% Hiviswako solution was painted on EC film prepared as mentioned above as adhesive glue, and the film was attached on EC basement layer. In addition, 2% Hiviswako 103 (Wako Pure Chemicals, Ltd.) solution was painted on the EC film as adhesive glue. 300 mg of Eudragit L-100 having a threshold dissolution pH of 6.0 and 25 µl of triethyl citrate were dissolved with 10 ml of a mixture of methylene chloride and ethyl alcohol (4:1), and the resultant mixture was casted onto Teflon plate (10.times. 10 cm), and was attached on the two layered EC films. By punching out the microcapsules with a preheated (at 90.degree. C.) stainless steal hole puncher having the same diameter of 5 G needle to obtain microcapsules, sustained-release malaria repellant capsules that can be adhesive to the skin for a long time were obtained.

Example 2

550 mg of Eudragit RS and 25 µl of triethyl citrate were dissolved with 5 ml of a mixture of methylene chloride and ethyl alcohol (4:1). The resulting mixture was casted on a Teflon plate of which size was 10×10 cm. By evaporating the solvent, Eudragit RS film of which thickness was about 50 µm, was obtained. Many dents were prepared by pressing the Eudragit RS film for 30 minutes with steel lump, 10 kg, on a aluminium plate, 9 cm×3.5 cm, coated with small amount of liquid paraffin and heated to 90° C., that has 1000 projections (20×50) of which diameter was 200 µm and height was 100 µm.

Eudragit RS film having many dents were obtained by removing from the aluminium plate after it was cooled. 50 nl of orange oil was filled into each of 1000 dents by a nanoinjector. The surface layer was a film made of Eudragit L-100. 2% Hiviswako 103 solution was spread on the surface of Eudragit L-100 film as adhesive glue, and was attached onto the. Eudragit RS film. By punching out with a preheated (at 90° C.) stainless steal hole puncher having the same diameter of 5 G needle to obtain microcapsules, sustained-release micro-capsules containing aroma chemicals were obtained.

Example 3

5 ml of distilled water was added to 150 mg of polyoxyethylene hydrogenated castor oil derivatives (HCO-60), 200 mg of citric acid and 150 mg of Hiviswako 103 and was mixed well in a motor with pestle. Thereafter, 200 µl of recombinant human granulocyte colony-stimulating factor (G-CSF) (500 µg/ml solution) was added and was mixed. The resulting mixture was uniformly spread on the surface of ethylcellulose film (10×10 cm), and was sandwiched between a surface layer, HP-55 film having a threshold dissolution pH of 5.5, after left for 2 hours at the room temperature. Mili-capsules were obtained by punching out with pre-heated (at 90° C.) stainless steal hole puncher of which diameter was 3.0 mm. The obtained capsules were treated with magnesium silicate powder and were filled in a #00 gelatin capsule. If necessary, the space was filled with sesame oil and the like and band seal was performed with the seam between capsule cap and body.

Example 4

According to the conventional method of Ooyama et al. (Japanese Journal of Transplantation, vol. 34, No. 4, pp. 174-185, 1999), pancreatic islet cells were obtained from rat and were filled in a micro-injector as a suspension with 1% carboxymethylcellulose. The islet cells suspension was injected by micro-injector into the dents (2 mm diameter and 1 mm depth) formed on a EC film that was prepared according to the method described in Example 1. HP-55 film was also prepared according to the method described in Example 1. The HP-55 film was treated with adhesive glue made of Hiviswako 103 and the obtained film was attached onto the EC film containing islet cells in the micro dents. Three layered hemispherical mili-capsules were obtained by cutting the peripheries of the dents (about 3 mm diameter) with laser beam.

INDUSTRIAL APPLICABILITY

According to the present invention, three layered hemispherical micro- and mili-capsules or films can be prepared with approximately 100% loading efficiency of the objective substance. The present invention can produce the three layers preparation in large amount by attaching and punching out the two layers, i.e., surface layer and basement layer, between which the objective substance is sandwiched.

The objective substance can be selected from not only liquid but also solid substances, i.e., drugs, aroma chemicals, mosquito repellant, dyes (especially cosmetic dyes), cells (living cells) or antigens.

By selecting the surface layer from different polymer films like pH-sensitive polymers having different dissolution threshold pHs, the system can have a targeting function to the adhesive site or can be adhesive to the skin surface for a long time after applied onto the skin. Otherwise, the system can be adhesive to the ocular mucosa, nasal mucosa, buccal mucosa and the like.

According to the present invention, three layered hemispheric micro- or mili-capsules and films can be produced in large amount. By selecting the suitable objective substance filled in the system, the application of the system cannot be limited. For example, the system can be applied to the pharmaceuticals, where the system containing recombinant proteins or peptides can improve the bioavailability of the objective proteins or peptides. In addition, the system can produce vaccine, artificial organ, sustained-release ocular preparation and sustained-release nasal preparation and the like. In the case of the cosmetic application, long-lasting lipstick and long-lasting eye shadow can be produced by using a cosmetic dye as an objective substance. For the purpose of moss repellant, the system can produce long-acting mosquito propellant that can be adhesive to the skin surface for a long time.

According to the present invention, three layered hemispherical micro- or mili-capsules and film preparation are provided, and their mass production method in a large scale has also been established.

According to the present invention, the objective substance can be filled in the micro- or mili-capsules with almost 100% loading efficiency, because objective substance is directly injected into the micro- or mili-dents formed on the basement film. Additionally, the obtained micro- or mili-capsules can have not only sustained-release function but also targeting function to the selected site, because the surface layer was prepared from various polymer films having different physicochemical characteristics and was attached onto the dents. Although the loading efficiency decreases a little, the preparation of the present invention can be produced in a large scale by heat-pressing and punching out the three layered film with hole puncher or laser beam after the objective substance is mixed with adhesive agent and is sandwiched between the surface and basement layers.

The invention claimed is:

1. A parenteral preparation having a three layer structure comprising:
   a basement layer composed of polymer;
   a carrying layer that contains an objective substance selected from drugs, aroma chemicals, mosquito repellant, dyes, cells, and antigens; and
   a surface layer;
   wherein the carrying layer is sandwiched between the basement layer and the surface layer, and the basement layer forms a hemispherical micro- or milli-sized container having a depth of 10-1000 μm and a diameter of 20-8000 μm, and the objective substance is in a liquid state filled in the micro- or milli-sized container to form the carrying layer; and
   wherein the basement layer, the carrying layer, and the surface layer are sealed.

2. The parenteral preparation according to claim 1, wherein the polymer of the basement layer is a water-insoluble polymer or biodegradable polymer.

3. The parenteral preparation according to claim 1, wherein the basement layer is a film made of ethylcellulose, cellulose acetate, polylactic acid, poly(lactic-co-glycolic acid), hydroxypropyl methylcellulose phthalate, or methacrylic acid copolymer S.

4. The parenteral preparation according to claim 1, wherein the objective substance contained in the carrying layer is granulocyte colony-stimulating factor (G-CSF), erythropoietin, interleukins, growth hormones, calcitonin, insulin, orange oil, N,N-diethyl-m-toluamide, botulinum toxin, or pancreatic islet cells.

5. The parenteral preparation according to claim 1, wherein the surface layer is made of pH-sensitive polymer, water-insoluble polymer, or biodegradable polymer.

* * * * *